(12) United States Patent
Reddy et al.

(10) Patent No.: US 9,580,440 B2
(45) Date of Patent: Feb. 28, 2017

(54) POLYMORPHS OF DARUNAVIR

(71) Applicant: Hetero Research Foundation, Hyderabad, Andrah Pradesh (IN)

(72) Inventors: Bandi Parthasaradhi Reddy, Andrah Pradesh (IN); Kura Rathnakar Reddy, Andrah Pradesh (IN); Dasari Muralidhara Reddy, Andrah Pradesh (IN); Rapolu Raji Reddy, Andrah Pradesh (IN); Kesireddy Subash Chander Reddy, Andrah Pradesh (IN); Bandi Vamsi Krishna, Andrah Pradesh (IN)

(73) Assignee: HETERO RESEARCH FOUNDATION (IN)

( * ) Notice: Subject to any disclaimer, the term of this patent is extended or adjusted under 35 U.S.C. 154(b) by 649 days.

(21) Appl. No.: 14/047,243

(22) Filed: Oct. 7, 2013

(65) Prior Publication Data

US 2014/0200356 A1   Jul. 17, 2014

Related U.S. Application Data

(62) Division of application No. 13/128,157, filed as application No. PCT/IN2009/000724 on Dec. 16, 2009, now abandoned.

(51) Int. Cl.
*A01N 43/08*  (2006.01)
*A61K 31/34*  (2006.01)
*C07D 493/00*  (2006.01)
*C07D 493/04*  (2006.01)
*A61K 9/20*   (2006.01)

(52) U.S. Cl.
CPC .......... *C07D 493/04* (2013.01); *A61K 9/2027* (2013.01); *A61K 9/2054* (2013.01); *A61K 31/34* (2013.01)

(58) Field of Classification Search
USPC .......................................... 514/470; 549/464
See application file for complete search history.

(56) References Cited

U.S. PATENT DOCUMENTS

| | | | |
|---|---|---|---|
| 3,876,632 A | | 4/1975 | Sturm et al. |
| 4,670,578 A * | | 6/1987 | Budavari et al. ............... 560/40 |
| 4,692,438 A | | 9/1987 | Hassall et al. |
| 5,315,016 A * | | 5/1994 | Hansen et al. ................. 549/298 |
| 6,248,775 B1 | | 6/2001 | Vazquez et al. |
| 7,649,010 B2 * | | 1/2010 | Chen et al. .................... 514/411 |
| 7,700,645 B2 | | 4/2010 | Vermeersch et al. |
| 8,921,415 B2 | | 12/2014 | Marom |
| 2003/0125336 A1 | | 7/2003 | Fleitz et al. |
| 2005/0250845 A1 | | 11/2005 | Vermeersch et al. |
| 2008/0269322 A1 | | 10/2008 | De Kock et al. |
| 2009/0111796 A1 * | | 4/2009 | Muto et al. .................... 514/221 |
| 2010/0094028 A1 | | 4/2010 | Lemaire et al. |
| 2011/0313035 A1 | | 12/2011 | Reddy et al. |
| 2012/0088808 A1 * | | 4/2012 | Pichler et al. ................ 514/412 |
| 2012/0288563 A1 | | 11/2012 | Reddy et al. |
| 2013/0072552 A1 | | 3/2013 | Parthasaradhi Reddy et al. |

FOREIGN PATENT DOCUMENTS

| | | |
|---|---|---|
| EP | 0715618 B1 | 12/1998 |
| WO | 9967417 A2 | 12/1999 |
| WO | 03106461 A2 | 12/2003 |
| WO | WO 03/106461 * | 12/2003 |
| WO | 2006067795 A2 | 6/2006 |
| WO | 2007054969 A2 | 5/2007 |
| WO | 2010086844 A1 | 8/2010 |
| WO | 2011073993 A1 | 6/2011 |

OTHER PUBLICATIONS

Vippagunta et. al. (Advanced Drug Delivery Reviews (2001) 48:3-26).*
U.S. Appl. No. 13/128,157, filed Jul. 6, 2011; Final Office Action of Oct. 22, 2013.
U.S. Appl. No. 13/128,157, filed Jul. 6, 2011; NonFinal Office Action of Jun. 10, 2013; 40 pages.
Ghosh et al.,; "Potent HIV Protease Inhibitors Incorporating High-Affinity P2-Ligands and (R)-(Hydroxyethylamino) Sulfonamide Isostere"; Bioorganic & Medicinal Chemistry Letters; 8; pp. 687-690; (1998).
International Search Report; International Application No. PCT/IN2009/000724; International Filing Date Dec. 16, 2009; Date of Mailing Jan. 3, 2011; 4 pages.
Vippagunta et al.; "Crystalline Solids"; Advanced Drug Delivery Reviews; 48; pp. 3-26; (2001).
U.S. Appl. No. 13/530,844, filed Jun. 22, 2012; final Office Action Mailed May 20, 2014; 20 pages.
Van Gyseghem et al.; "Solid State Characterization of the Anti-HIV Drug TMC114:Interconversion of Amorphous TMC114,TMC114 Ethanolate and Hydrate"; European Journal of Pharmaceutical Sciences; 38; pp. 489-497; (2009).
U.S. Appl. No. 13/530,844, filed Jun. 22, 2012; NonFinal Office Action of Jan. 7, 2014; 31 pages.
Yu, Lian; "Amorphous Pharmaceutical Solids: Preparation, Characterization and Stabilization"; Advanced Drug Delivery Reviews; 48; pp. 27-42; (2001).

(Continued)

*Primary Examiner* — Marcos Sznaidman
(74) *Attorney, Agent, or Firm* — Cantor Colburn LLP

(57) ABSTRACT

The present invention provides novel solvated forms of darunavir and processes for their preparation. The present invention also provides novel processes for the preparation of darunavir amorphous form and pharmaceutical compositions comprising it. Thus, for example, darunavir 2-methyl-2-butanol solvate was dissolved in methylene dichloride, distilled under vacuum at 45° C. to obtain a residue, cyclohexane was added to the residue and stirred for 30 hours at 20 to 25° C., and the separated solid was filtered, washed with cyclohexane and dried under vacuum at 50° C. for 12 hours to yield darunavir amorphous form.

4 Claims, 3 Drawing Sheets

(56) References Cited

OTHER PUBLICATIONS

Morissette et al.; in Advance Drug Delivery Reviews; 56; pp. 275-300; (2004).
Bastin et al. in Organic Process & Development 4, pp. 427-435; (2000).
Chemist's Companion, A. J. gordon and R. A. Ford, Wiley-Interscience, 1972.

* cited by examiner

POLYMORPHS OF DARUNAVIR

CROSS-REFERENCE TO RELATED APPLICATIONS

This application is a divisional of U.S. application Ser. No. 13/128,157 filed Jul. 6, 2011, which is a 371 of PCT/IN2009/000724, filed Dec. 16, 2009, which are incorporated by reference herein in their entirety.

FIELD OF THE INVENTION

The present invention provides novel solvated forms of darunavir and processes for their preparation. The present invention also provides novel process for preparation of darunavir amorphous form and pharmaceutical composition comprising it.

BACKGROUND OF THE INVENTION

Virus-encoded proteases, which are essential for viral replication, are required for the processing of viral protein precursors. Interference with the processing of protein precursors inhibits the formation of infectious virions. Accordingly, inhibitors of viral proteases may be used to prevent or treat chronic and acute viral infections. Darunavir has HIV protease inhibitory activity and is particularly well suited for inhibiting HIV-1 and HTV-2 viruses. Among them darunavir, chemically (1S,2R,3'R,3'aS,6'aR)-[3'-hexahydrofuro[2,3-b]furanyl-[3-(4-aminobenzenesulfonyl)isobutylamino]-1-benzyl-2-hydroxypropyl]carbamate. Darunavir is represented by the following structure:

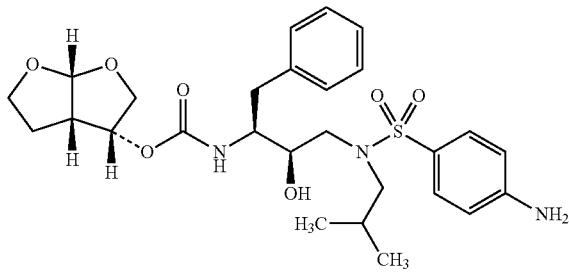

Processes for the preparations of darunavir were disclosed in EP 715618, WO 99/67417, U.S. Pat. No. 6,248,775, and in Bioorganic and Chemistry Letters, Vol. 8, pp. 687-690, 1998, "Potent HIV protease inhibitors incorporating high-affinity P2-igands and (R)-(hydroxyethylamino)sulfonamide isostere", all of which are incorporated herein by reference.

Polymorphism is defined as "the ability of a substance to exist as two or more crystalline phases that have different arrangement and/or conformations of the molecules in the crystal lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Darunavir can exist in different polymorphic forms, which differ from each other in terms of stability, physical properties, spectral data and methods of preparation.

U.S. Patent Application No. 2005/0250845 described Amorphous Form, Form A (ethanolate), Form B (hydrate), Form C (methanolate), Form D (acetonate), Form E (dichloromethanate), Form F (ethylacetate solvate), Form G (1-ethoxy-2-propanolate), Form H (anisolate), Form I (tetrahydrofuranate), Form J (isopropanolate) and Form K (mesylate) of darunavir.

One object of the present invention is to provide novel solvated forms of darunavir and processes for their preparation.

Another object of the present invention is to provide a novel process for preparation of darunavir amorphous form and pharmaceutical compositions comprising them.

SUMMARY OF THE INVENTION

In one aspect, the present invention provided darunavir $C_5$-$C_8$ alcohol solvate.

In another aspect, the present invention provides a process for preparing darunavir $C_5$-$C_8$ alcohol solvate, which comprises crystallizing darunavir $C_5$-$C_8$ alcohol solvate from a solution of darunavir in $C_5$-$C_8$ alcohol solvent.

In another aspect, the present invention provides a process for preparing darunavir amorphous form, which comprises:
 a) dissolving darunavir in a solvent;
 b) removing the solvent from the solution obtained in step (a) to obtain a residue;
 c) slurrying the residue obtained in step (b) with aliphatic solvent or aromatic solvent; and
 d) isolating darunavir amorphous form.

In yet another aspect, the present invention provides a pharmaceutical composition comprising darunavir amorphous form and a pharmaceutically acceptable excipient.

X-ray powder diffraction spectrum was measured on a bruker axs D8 advance X-ray powder diffractometer having a copper-K$\alpha$ radiation. Approximately 1 gm of sample was gently flattered on a sample holder and scanned from 2 to 50 degrees two-theta, at 0.02 degrees to theta per step and a step of 10.4 seconds. The sample was simply placed on the sample holder. The sample was rotated at 30 rpm at a voltage 40 KV and current 35 mA.

DETAILED DESCRIPTION OF THE INVENTION

According to one aspect of the present invention, there is provided darunavir $C_5$-$C_8$ alcohol solvate.

According to another aspect of the present invention, there is provided a process for preparing darunavir $C_5$-$C_8$ alcohol solvate, which comprises crystallizing darunavir $C_5$-$C_8$ alcohol solvate from a solution of darunavir in $C_5$-$C_8$ alcohol solvent.

Solvates can occur in different ratios of solvation. The ratio of darunavir to the $C_5$-$C_8$ alcohol solvent may range between 1:0.3 and 1:1.3. In particular, the ratio may range from about 0.5 to about 1 molecules of $C_5$-$C_8$ alcohol solvent per 1 molecule of darunavir, preferably the ratio is 1 molecule of $C_5$-$C_8$ alcohol solvent per 1 molecule of darunavir.

The $C_5$-$C_8$ alcohol solvent is selected from 2-methyl-2-butanol or n-pentanol.

Figure 1:
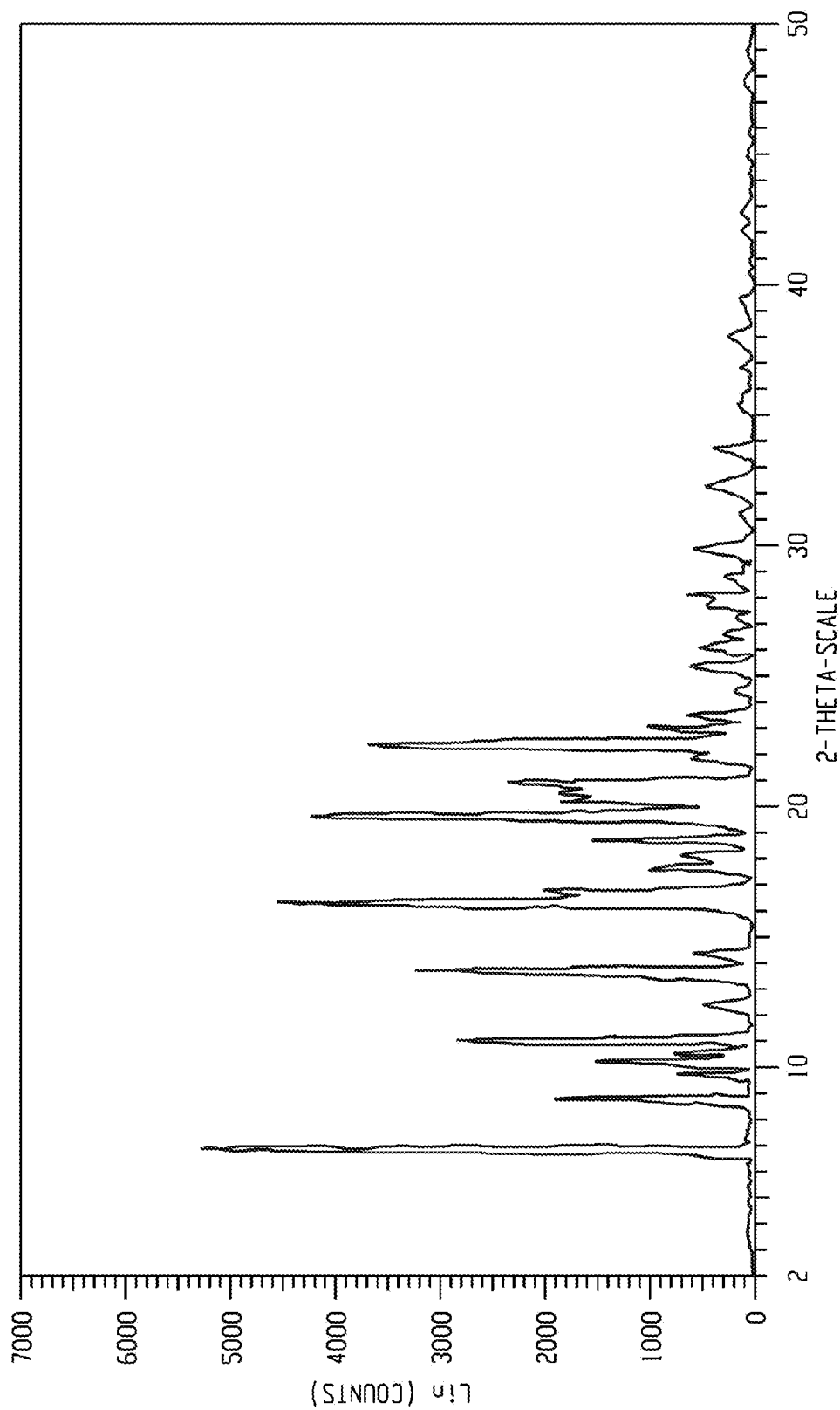
FIG. 1 is X-ray powder diffraction spectrum of darunavir 2-methyl-2-butanol solvate.

Darunavir 2-methyl-2-butanol solvate characterized by peaks in the powder x-ray diffraction spectrum having 2θ angle positions at about 6.8, 8.8, 11.1, 13.7, 16.3, 16.7, 19.6, 20.9 and 22.3±0.2 degrees. The powdered x-ray diffractogram (PXRD) of darunavir 2-methyl-2-butanol solvate is shown in FIG. 1.

Figure 2:
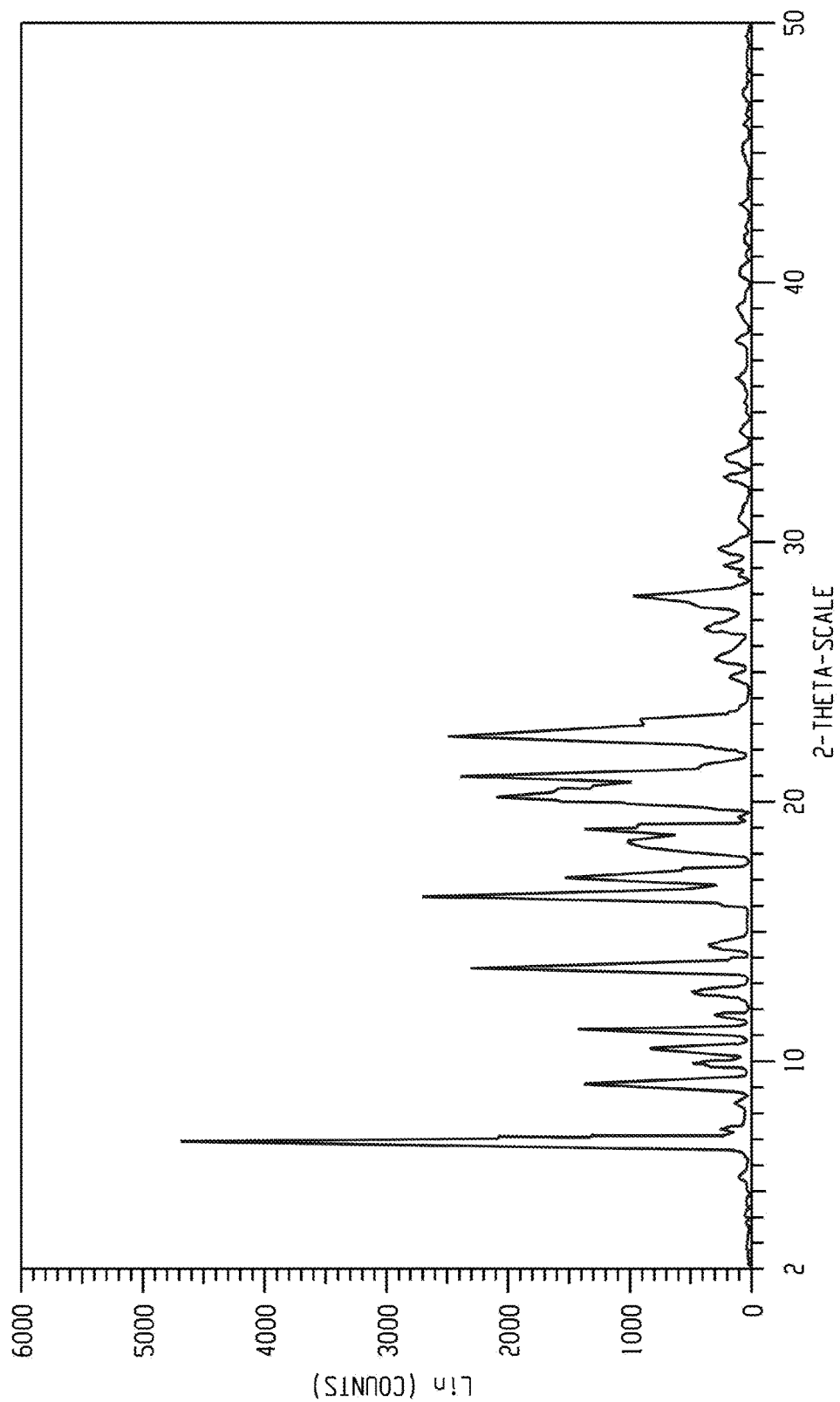
FIG. 2 is X-ray powder diffraction spectrum of darunavir n-pentanol solvate.
Figure 3:
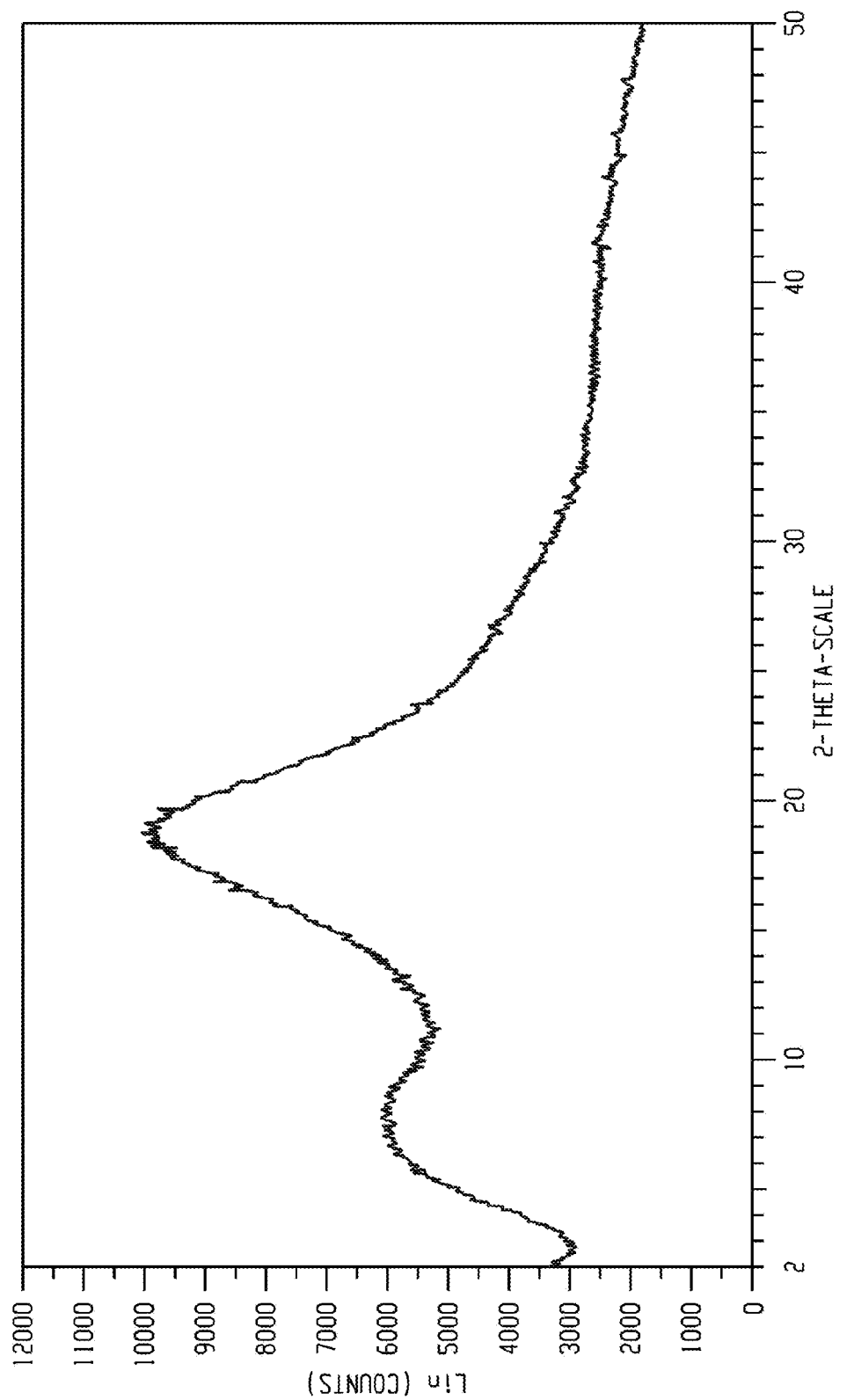
FIG. 3 is X-ray powder diffraction spectrum of darunavir amorphous form.

Darunavir n-pentanol solvate characterized by peaks in the powder x-ray diffraction spectrum having 2θ angle positions at about 6.9, 9.1, 11.2, 13.7, 16.4, 17.1, 20.3, 20.6, 21.1 and 22.6±0.2 degrees. The powdered x-ray diffractogram (PXRD) of darunavir n-pentanol solvate is shown in FIG. 2.

The solvates of the present invention are useful intermediates for obtaining pure darunavir. The solvates of darunavir of the present invention can be used to obtain known polymorphs of darunavir.

According to another aspect of the present invention, there is provided a process for the preparation of darunavir amorphous form, which comprises:
a) dissolving darunavir in a solvent;
b) removing the solvent from the solution obtained in step (a) to obtain a residue;
c) slurrying the residue obtained in step (b) with aliphatic solvent or aromatic solvent; and
d) isolating darunavir amorphous form.

Darunavir used in step (a) is darunavir in any solvated or hydrated- or anhydrous form.

Preferably, darunavir used in step (a) is darunavir $C_5$-$C_8$ alcohol solvate such as 2-methyl-2-butanol solvate or n-pentanol solvate.

The solvent used in step (a) may be a solvent or mixture of solvents selected from the group consisting of a dichloromethane, ethylene dichloride, chloroform and ethyl acetate. Preferable solvent is dichloromethane.

The distillation of the solvent may be carried out in step (b) at atmospheric pressure or at reduced pressure. The distillation may preferably be carried out until the solvent is almost completely distilled off.

The aliphatic solvent or aromatic solvent used in step (c) may be a solvent or a mixture of solvents selected from the group consisting of a cyclohexane, hexane, n-heptane, toluene and xylene. Preferable aliphatic solvent is cyclohexane.

The isolation of darunavir amorphous form may be performed by conventional techniques such as centrifugation and filtration.

According to another aspect of the present invention, there is provided a pharmaceutical composition comprising a darunavir amorphous form and a pharmaceutically acceptable excipient.

The pharmaceutically acceptable inert carrier which can be used may be a solid dosage forms.

The solid dosage forms for oral administration may include capsules, tablets, pills, powders and granules.

The invention will now be further described by the following examples, which are illustrative rather than limiting.

PREPARATIVE EXAMPLE

Preparation of Darunavir

To a mixture of (3R,3aS,6aR)-hexandrofuro[2,3-b] furan-3-ol (25 gm) and acetonitrile (180 ml) was added disuccinimidyl carbonate (56 gm) and pyridine (46 gm) at 25 to 30° C. The mixture was stirred for 1 hour at 25 to 30° C. and cooled to 0° C. A solution of 4-amino-N-((2R,3S)-3-amino-2-hydroxy-4-phenylbutyl)-N-(isobutyl)benzene sulfonamide (70 gm) in acetonitrile (300 ml) was added to the reaction mass at 0 to 5° C. for 30 minutes. To the reaction mass was added triethylamine (19 gm) and monomethylamine (3 gm) at 0 to 5° C., the temperature was slowly raised to 25 to 30° C. and stirred for 22 hours. Distilled off the solvent completely under vacuum at 45° C. to obtain a residue and to the residue was added ethyl acetate (250 ml). The ethyl acetate layer was washed with 10% sodium bicarbonate (100 ml), 2% sulfuric acid (100 ml), 10% sodium sulfate (100 ml) and 10% sodium chloride solution (100 ml). The layer was dried over sodium sulfate. The layer was treated with carbon and distilled off the solvent under vacuum at below 45° C. to obtain 85 gm of darunavir.

EXAMPLES

Example 1

Preparation of darunavir 2-methyl-2-butanol solvate

Darunavir (85 gm) as obtained in preparative example was added to 2-methyl-2-butanol (50 ml) and distilled off the solvent under vacuum at below 45° C. to obtain a residue. To the residue was added 2-methyl-2-butanol (150 ml) and heated to 50° C. The reaction mass was slowly cooled to room temperature and stirred for 24 hours. The reaction mass further cooled to 0° C. and stirred for 1 hour at 0 to 5° C. The separated solid was filtered, washed with 2-methyl-2-butanol and dried the solid under vacuum at 50° C. to obtain 60 gm of darunavir 2-methyl-2-butanol solvate.

Example 2

Preparation of Darunavir N-Pentanol Solvate

Darunavir (85 gm) as obtained in preparative example was added to n-pentanol (50 ml) and distilled off the solvent under vacuum at below 45° C. to obtain a residue. To the residue was added n-pentanol (150 ml) and heated to 50° C. The reaction mass was slowly cooled to room temperature and stirred for 24 hours. The reaction mass further cooled to 0° C. and stirred for 1 hour at 0 to 5° C., filtered. The solid obtained was washed with n-pentanol and dried the solid under vacuum at 50° C. to obtain 61 gm of darunavir n-pentanol solvate.

Example 3

Preparation of Darunavir Amorphous Form

Darunavir 2-methyl-2-butanol solvate (5 gm) as obtained in example 1 was dissolved in methylene dichloride (50 ml), methylene dichloride layer was dried over sodium sulfate. The layer was treated with carbon and distilled off the solvent under vacuum at 45° C. to obtain foam like residue. Cyclohexane (2×25 ml) was added to the residue, distilled off the solvent and the residue was collected. To the residue obtained was added cyclohexane (50 ml), stirred for 30 hours at 20 to 25° C. The separated solid was filtered, washed with cyclohexane and then dried under vacuum at 50° C. for 12 hours to obtain 4.2 gm of darunavir amorphous form.

Example 4

Preparation of Darunavir Amorphous Form

Darunavir n-pentanol solvate (5 gm) as obtained in example 2 was dissolved in methylene dichloride (50 ml), methylene dichloride layer was dried over sodium sulfate. The layer was treated with carbon and distilled off the solvent under vacuum at 45° C. to obtain foam like residue. Cyclohexane (2×25 ml) was added to the residue, distilled off the solvent and the residue was collected. To the residue obtained was added cyclohexane (50 ml), stirred for 30 hours at 20 to 25 C, filtered, washed with cyclohexane and dried under vacuum at 50° C. for 12 hours to obtain 4.2 gm of darunavir amorphous form.

Example 5

Preparation of Darunavir Amorphous Form

Example 3 was repeated using darunavir ethanolate form A instead of darunavir 2-methyl-2-butanol solvate to obtain darunavir amorphous form.

Example 6

Preparation of Darunavir Amorphous Form

Example 3 was repeated using darunavir hydrated form B instead of darunavir 2-methyl-2-butanol solvate to obtain darunavir amorphous form.

The invention claimed is:

1. A darunavir 2-methyl-2-butanol solvate characterized by peaks in the powder x-ray diffraction spectrum having 2θ angle positions at 6.8, 8.8, 11.1, 13.7, 16.3, 16.7, 19.6, 20.9 and 22.3±0.2 degrees.

2. The darunavir 2-methyl-2-butanol solvate of claim 1, characterized by the powder x-ray diffractogram of FIG. 1.

3. A darunavir n-pentanol solvate characterized by peaks in the powder x-ray diffraction spectrum having 2θ angle positions at 6.9, 9.1, 11.2, 13.7, 16.4, 17.1, 20.3, 20.6, 21.1 and 22.6±0.2 degrees.

4. The darunavir n-pentanol solvate of claim 3, characterized by the powder x-ray diffractogram of FIG. 2.

* * * * *